United States Patent
Till

(10) Patent No.: US 9,056,146 B2
(45) Date of Patent: Jun. 16, 2015

(54) METHOD OF TREATING THE INSIDE SURFACES OF A CLEAN ROOM AND TREATING A ROTARY BEVERAGE BOTTLE BLOW-MOLDING ARRANGEMENT AND BLOW-MOLDING BEVERAGE BOTTLES FROM PREFORMS AND AN ARRANGEMENT FOR PERFORMING THE METHOD

(75) Inventor: Volker Till, Hofhiem am Taunus (DE)

(73) Assignee: KHS GmbH, Dortmund (DE)

( * ) Notice: Subject to any disclaimer, the term of this patent is extended or adjusted under 35 U.S.C. 154(b) by 955 days.

(21) Appl. No.: 12/578,178

(22) Filed: Oct. 13, 2009

(65) Prior Publication Data

US 2010/0089009 A1     Apr. 15, 2010

Related U.S. Application Data

(63) Continuation-in-part of application No. PCT/EP2008/002602, filed on Apr. 2, 2008.

(30) Foreign Application Priority Data

Apr. 13, 2007   (DE) .......................... 10 2007 017 938

(51) Int. Cl.
| | | |
|---|---|---|
| *A61L 2/10* | (2006.01) | |
| *A61L 2/08* | (2006.01) | |
| *B29C 49/42* | (2006.01) | |
| *B29C 49/06* | (2006.01) | |

(Continued)

(52) U.S. Cl.
CPC . *A61L 2/087* (2013.01); *A61L 2/10* (2013.01); *A61L 2202/23* (2013.01); *B29C 49/06* (2013.01); *B29C 49/36* (2013.01); *B29C 49/42* (2013.01); *B29C 2791/005* (2013.01); *B29K 2067/00* (2013.01)

(58) Field of Classification Search
CPC ................................................. A61L 2/08–2/12
USPC ........... 53/425, 426, 433, 456, 452, 559, 561;
422/20, 21, 22, 24; 250/492.1
IPC ..................................... A61L 2/10; B67C 7/00
See application file for complete search history.

(56) References Cited

U.S. PATENT DOCUMENTS 2,546,205 A * 3/1951 Zimmermann ................. 53/279
3,809,768 A    5/1974 Berry (Continued)

FOREIGN PATENT DOCUMENTS

| DE | 3701915 A1 * | 8/1988 | ............... B67C 7/00 |
| DE | 29503830 U1 | 6/1995 | |

(Continued)

OTHER PUBLICATIONS

International Search Report PCT/EP2007/002602 and English translation thereof.

(Continued)

*Primary Examiner* — Stephen F Gerrity
(74) *Attorney, Agent, or Firm* — Nils H. Ljungman & Associates

(57) ABSTRACT

Container-producing arrangement which includes a blow-molding machine and at least one radiation emitter disposed at, on, or adjacent the blow-molding machine in order to sterilize a portion of the blow-molding machine and/or a portion of a housing which surrounds the container-producing arrangement.

19 Claims, 5 Drawing Sheets

(51) Int. Cl.
*B29C 49/36* (2006.01)
*B29K 67/00* (2006.01)

(56) References Cited

U.S. PATENT DOCUMENTS

| | | | |
|---|---|---|---|
| 4,309,388 A * | 1/1982 | Tenney et al. | 422/24 |
| 4,877,964 A * | 10/1989 | Tanaka et al. | 250/455.11 |
| 5,129,212 A * | 7/1992 | Duffey et al. | 53/426 |
| 5,433,920 A * | 7/1995 | Sizer et al. | 422/24 |
| 5,669,208 A * | 9/1997 | Tabaroni et al. | 53/453 |
| 5,928,607 A * | 7/1999 | Frisk | 422/29 |
| 5,958,336 A * | 9/1999 | Duarte | 422/24 |
| 6,039,922 A * | 3/2000 | Swank et al. | 422/24 |
| 6,183,691 B1 * | 2/2001 | Swank et al. | 422/24 |
| 6,351,924 B1 * | 3/2002 | Gustafsson et al. | 53/425 |
| 6,433,344 B1 * | 8/2002 | Salisbury et al. | 250/492.1 |
| 6,562,281 B1 | 5/2003 | Marchau et al. | |
| 6,565,791 B1 * | 5/2003 | Laurent | 264/455 |
| 6,818,068 B1 | 11/2004 | Guiffant et al. | |
| 7,111,649 B2 * | 9/2006 | Py | 141/11 |
| 2001/0010145 A1 * | 8/2001 | Tawa et al. | 53/425 |
| 2002/0155027 A1 * | 10/2002 | Gutman | 422/24 |
| 2005/0118057 A1 | 6/2005 | Quetel et al. | |
| 2005/0158218 A1 * | 7/2005 | Dumargue et al. | 422/121 |
| 2005/0223988 A1 | 10/2005 | Behle et al. | |
| 2006/0104859 A1 * | 5/2006 | Tribelsky | 422/24 |
| 2006/0192140 A1 * | 8/2006 | Nablo et al. | 250/492.1 |
| 2006/0228251 A1 * | 10/2006 | Schneberger et al. | 422/24 |
| 2007/0018115 A1 * | 1/2007 | Naka et al. | 250/454.11 |
| 2007/0253861 A1 * | 11/2007 | Naka et al. | 422/22 |
| 2007/0258851 A1 * | 11/2007 | Fogg et al. | 422/24 |
| 2010/0047120 A1 * | 2/2010 | Adriansens et al. | 422/22 |

FOREIGN PATENT DOCUMENTS

| | | | |
|---|---|---|---|
| DE | 29508864 | | 11/1995 |
| DE | 19520925 A1 | | 12/1996 |
| DE | 19909488 | | 9/2000 |
| DE | 696 24 509 | | 2/2003 |
| DE | 10140906 | | 3/2003 |
| DE | 10140906 A1 | | 3/2003 |
| DE | 10236683 | | 2/2004 |
| DE | 102004061230 | | 7/2006 |
| DE | 102005015565 | | 10/2006 |
| DE | 102005026645 A1 | | 2/2007 |
| DE | 202006011943 U1 | | 4/2007 |
| EP | 0 464 933 | | 1/1992 |
| EP | 0895816 | | 2/1999 |
| EP | 1 507 894 B1 | | 12/2005 |
| FR | 2 815 542 | | 4/2002 |
| FR | 2 838 076 A | | 10/2003 |
| JP | 63281936 A | | 11/1988 |
| JP | 4147824 A | | 5/1992 |
| JP | 10167226 | | 6/1998 |
| JP | H1016726 A | | 6/1998 |
| JP | 11114029 A * | 4/1999 | A61L 2/10 |
| JP | 11137645 A | | 5/1999 |
| JP | H11137645 A | | 5/1999 |
| JP | 2000309396 A * | 11/2000 | B67C 7/00 |
| JP | 2001171622 A * | 6/2001 | A61L 2/10 |
| JP | 2001510104 | | 7/2001 |
| JP | 2001225814 | | 8/2001 |
| JP | 2002114293 A * | 4/2002 | A61L 2/10 |
| JP | 2002179191 A * | 6/2002 | A61L 2/10 |
| JP | 2005 008243 A | | 1/2005 |
| JP | 2005528242 | | 9/2005 |
| JP | 2006013049 | | 1/2006 |
| WO | WO 97/18154 | | 5/1997 |
| WO | WO 98/47770 | | 10/1998 |
| WO | WO 99/03667 A | | 1/1999 |
| WO | WO 00/58631 A | | 10/2000 |
| WO | WO 01/31680 | | 5/2001 |
| WO | WO 03/100116 A | | 12/2003 |
| WO | WO 2008/070956 | | 6/2008 |

OTHER PUBLICATIONS

German Search Report 10 2007 017 938.5 (Sep. 5, 2007).
German Search Report 10 2007 017 938.5 (Mar. 3, 2009).

* cited by examiner

METHOD OF TREATING THE INSIDE SURFACES OF A CLEAN ROOM AND TREATING A ROTARY BEVERAGE BOTTLE BLOW-MOLDING ARRANGEMENT AND BLOW-MOLDING BEVERAGE BOTTLES FROM PREFORMS AND AN ARRANGEMENT FOR PERFORMING THE METHOD

This application is a Continuation-In-Part application of International Patent Application No. PCT/EP2008/002602, filed on Apr. 2, 2008, which claims priority from Federal Republic of Germany Patent Application No. 10 2007 017 938.5, filed on Apr. 13, 2007. International Patent Application No. PCT/EP2008/002602 was pending as of the filing date of this application. The United States was an elected state in International Patent Application No. PCT/EP2008/002602.

BACKGROUND

1. Technical Field

The present application relates to a container-producing apparatus for producing plastics material containers from preforms, in one possible embodiment bottles, small receptacles (kegs) and other containers made from PET, said apparatus including a blow molding machine and suitable conveying devices, wherein at least one radiation emitter is mounted at the blow molding machine or on said blow molding machine and/or a radiation emitter is directed onto at least one part region of the blow molding machine. In addition, the present application includes a corresponding sterilizing method for blow molding machines.

2. Background Information

Background information is for informational purposes only and does not necessarily admit that subsequently mentioned information and publications are prior art.

Some container-producing apparatuses mold bottles, for example, from preforms by means of a stretch blow molding machine.

Increasingly, there is a requirement to achieve greater and greater levels of cleanliness or aseptic conditions in the production and filling of containers and bottles. It is usual for the preform to have been cleaned of possible adhesions already by, for example, passing a current of ionized air into the interior. Some apparatuses and methods where bottles are coated and at the same time sterilized by a plasma being ignited under vacuum. Additional apparatuses and methods are known. Wet and dry aseptic methods are known for filler units.

The processing steps can or may be carried out before or after the blow molding machine, as up to now it has not been possible to operate the blow molding machine itself in a sterile manner.

OBJECT OR OBJECTS

Consequently, it is an object of the present application to provide a method that is sterile in its entirety.

SUMMARY

This object is achieved according to the present application through features of a container-producing apparatus for producing plastics material containers from preforms, in one possible embodiment bottles, small receptacles (kegs) and other containers made from PET. The apparatus includes a blow molding machine and suitable conveying devices. At least one radiation emitter is mounted at the blow molding machine or on said blow molding machine and/or a radiation emitter is directed onto at least one part region of the blow molding machine and/or at least onto a part face of the inside surfaces of the housing surrounding the container-producing apparatus. This object is achieved according to the present application through the features of a method for producing plastics material containers from preforms, in one possible embodiment bottles, small vessels and other containers made from PET. A container-producing apparatus according to the present application is used in order to sterilize and/or to keep sterile permanently or substantially permanently at least one part of the surfaces of the container-producing apparatus and/or the at least one part of the inside surfaces of the housing surrounding the container-producing apparatus.

The container-producing apparatus according to the present application for producing plastics material containers, in one possible embodiment bottles, small receptacles (kegs) and other containers made from PET, from preforms, includes a blow molding machine and suitable conveying devices, wherein at least one radiation emitter is mounted in the vicinity of the blow molding machine, at the blow molding machine or on said blow molding machine, and/or a radiation emitter is directed onto at least one part region of the blow molding machine or its housing. The radiation emitter is in one possible embodiment an electron emitter or UV emitter. The UV emitter is in one possible embodiment one for pulsed UV light. It is possible, depending on the radiation task, to use a plurality of identical or different-type radiation emitters. Consequently, it is possible to sterilize at least a part of the surfaces of the container-producing apparatus and/or the area surrounding the container-producing apparatus and/or to keep it sterile.

In at least one possible embodiment of the present application, in the case of a rotary blow molding machine, the radiation emitters are mounted on or at least one of the rotating elements so that the radiation emitter rotates with the carousel of the blow molding machine. In this way, the number of emitters can be reduced and the distribution of radiation in the area increased. In this case, at least one radiation emitter can be mounted on the carousel or star wheel supporting or supplying the blow molds, said radiation emitter rotating in normal operation with said carousel or star wheel.

In at least one possible embodiment, at least one part of the surfaces of the container-producing apparatus is designed so as to be electrostatically chargeable in order to guide the electron beams in this manner in normal operation. In this case, in one possible embodiment, parts of the surfaces of the container-producing apparatus, in one possible embodiment of the blow molding machine are designed so as to be positively electrostatically chargeable in order to attract electrons and/or electron beams in this manner through the potential difference. Surfaces that are difficult to access, for example, can be impinged upon with the electron beam in this way.

In at least one possible embodiment of the present application, at least a portion of the container-producing apparatus may comprise positive electric-potential, potential positive voltage, and/or potential positive charge, in order to attract electrons and/or electron beams.

In a further development of the container-producing apparatus, a sterilizing unit is provided upstream of the container-producing apparatus, in which sterilizing unit the preforms are sterilized upstream of the blow molding machine by means of radiation emitters. To this end, the sterilizing unit can include one or more radiation emitters, in one possible embodiment electron emitters, which are introducible into the opening in the preform.

In one possible embodiment, the container-producing apparatus and the sterilizing unit are directly interconnected so that said container-producing apparatus and sterilizing unit form a common, closed area. In addition, a filler unit can be positioned downstream of the container-producing apparatus, said filler unit being connected directly and in a sealing manner to the container-producing apparatus so that, in this specific embodiment, the sterilizing unit for preforms, the container-producing apparatus and the filler unit form a substantially common area constructed in a modular manner. In an analogous manner, a filler unit can be provided downstream of the container-producing apparatus without a sterilizing unit for preforms being provided, the filler unit being directly connected to the container-producing apparatus and said filler unit and container-producing unit forming a common area in this manner.

The present application also relates to a method for producing plastics material containers from preforms, said method using a container-producing apparatus in one of the abovementioned variants. Bottles, small receptacles (kegs) and other containers made from PET or other suitable plastics materials are possible as plastics material containers.

In one possible embodiment, in this case, the container-producing apparatus is operated with a sterilizing unit for preforms and/or a filler unit as a common sterile area. In at least one possible embodiment of the present application, in the transition region between the filler unit, container-producing apparatus and/or the sterilizing unit for preforms, one or more locks and/or additional sterilizing steps are provided. In one possible embodiment, a part of the apparatuses and/or of the containers is sterilized using a wet method. In at least one possible embodiment of the present application, the region that is sterilized with the wet method is where the upper end of said region is deeper than the openings in the preforms and/or containers and extends downwards as far as the ground.

The above-discussed embodiments of the present invention will be described further herein below. When the word "invention" or "embodiment of the invention" is used in this specification, the word "invention" or "embodiment of the invention" includes "inventions" or "embodiments of the invention", that is the plural of "invention" or "embodiment of the invention". By stating "invention" or "embodiment of the invention", the Applicant does not in any way admit that the present application does not include more than one patentably and non-obviously distinct invention, and maintains that this application may include more than one patentably and non-obviously distinct invention. The Applicant hereby asserts that the disclosure of this application may include more than one invention, and, in the event that there is more than one invention, that these inventions may be patentable and non-obvious one with respect to the other.

DESCRIPTION OF EMBODIMENT OR EMBODIMENTS

Figure 1:
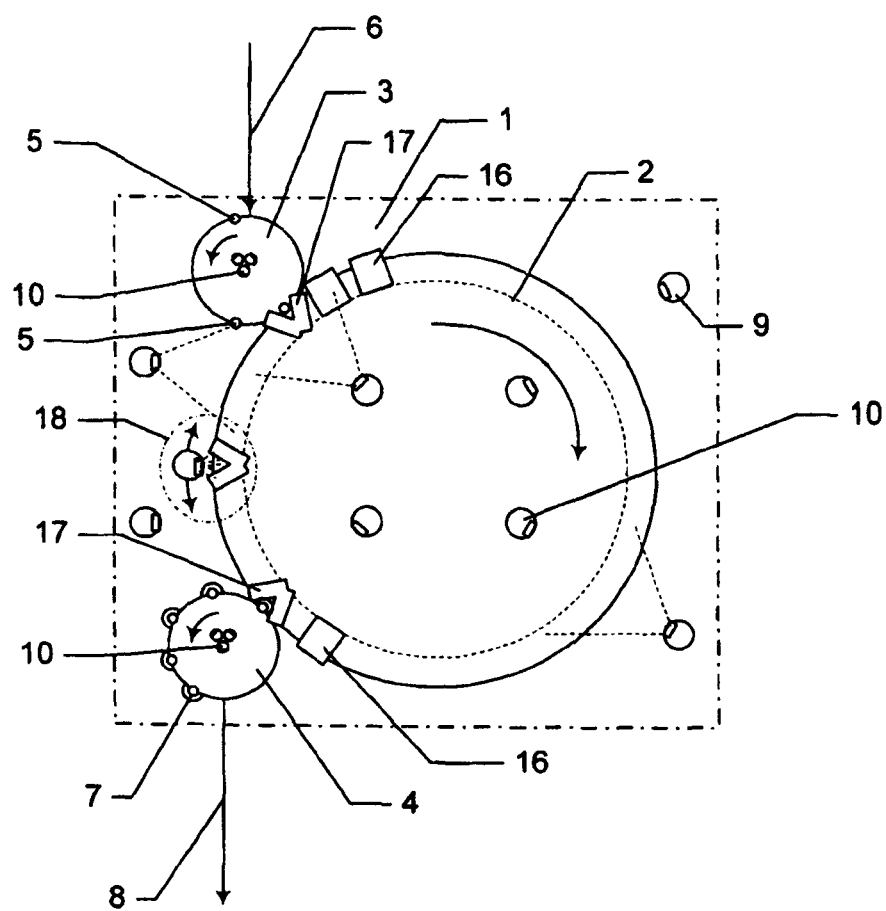
FIG. 1 shows a representation of a top view of the container-producing apparatus.

The container-producing apparatus 1, framed by the dot dash line, includes a carousel 2, a supply star 3 and an outlet star 4. Further details, such as a heating device, blow molds, etc. are known and are not represented in FIG. 1. The preforms 5 and the molded bottles 7 are conveyed first and foremost in a suspended manner, to which end they are retained at the neck in a known manner by means of grippers or holders ("neck handling"). The preforms 5 are supplied to the supply star 3 by means of the conveying path 6 and are transferred from said supply star to the carousel 2. Cavities 16 are positioned on the periphery of the carousel 2, said cavities for reasons of clarity being shown in a partial manner and the stretch/blow molding procedure being carried out in a known manner in said cavities. An open cavity 17 is shown opposite the supply star 3, and in the same way there is one opposite the outlet star 4, which takes over the full blown bottle.

After the blowing process at the rotary-type blow molding machine, the fully molded bottles 7 are removed from the outlet star 4 and guided out of the container-producing apparatus by means of the conveying path 8. A plurality of radiation emitters are positioned in the container-producing apparatus 1. The stationary radiation emitters 9 are positioned at the edge of the container-producing apparatus 1 and radiate in the direction of the installed components. Some radiation emitters are oriented such that they are directed onto the walls that form the housing, including the ceiling and the floor. The direction of radiation is indicated by a dot dash line.

A plurality of radiation emitters 10 are positioned in each case on the supply star 3 and on the outlet star 4 and on the central carousel 2, said radiation emitters rotating together with the star or the carousel. Intensive, multiply diffused radiation is generated in this manner.

Electron emitters are provided in the example shown, a combination with, for example, pulsed UV lamps being a good idea. The station 18, surrounded by a dot dash line, provides the inside sterilization of the cavity 17. In this case, the emitter is positioned in one possible embodiment close to the carousel 2 and can follow the carousel 2 or the open cavity 17 over a certain path in order to improve the sterilizing effect in the interior of the cavity 17.

Figure 2:
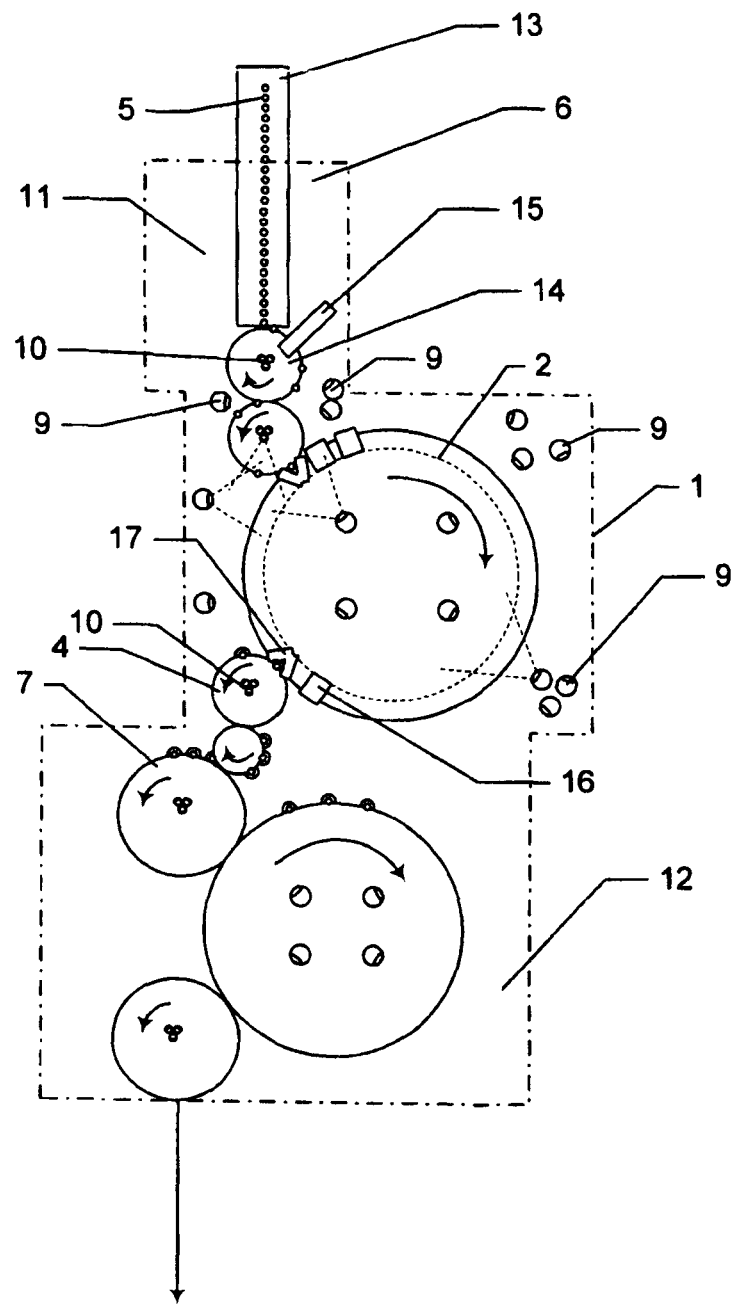
FIG. 2 show a representation of a top view of a sterilizing unit for preforms, a container-producing apparatus and a filler unit.

FIG. 2 shows the container-producing apparatus 1 shown in FIG. 1 and described above in a common housing with a sterilizing unit 11 for preforms 5 and a filler unit 12. This so-called modular type of construction in one possible embodiment is very compact and consequently economical, as intermediate cleaning steps and some conveying steps are omitted. The references are identical to those in FIG. 1 unless something to the contrary is stated.

The preforms 5 pass via a hot and supply unit 13 (not shown in any more detail) for the preforms 5 into the sterilizing unit 11, where they are taken over by processing stars 14. A sterilizing device 15 is positioned on the periphery of the processing star 14. For sterilizing a preform 5, a sterilizing probe is introduced into the preform, at least one radiation emitter being positioned at the periphery and/or tip of said sterilizing probe. To this end, radiation densities of fifteen to thirty kJ/kg are necessary and/or desired.

In the possible embodiment represented, stationary radiation emitters 9 are positioned in the region of the sterilizing unit 11, downstream of the sterilizing device 15, on both sides of the transfer region from the processing star 14 to the supply star 3 of the container-producing apparatus 1. The filler unit 12 connects to the container-producing apparatus 1 as another unit in the same modular system. Stationary radiation emitters 9 and rotating radiation emitters 10 are also provided here.

The container-producing apparatus 1 according to the present application and the method are described in an one possible embodiment, many variants according to the same principle being possible. In one possible embodiment, a pre-heat unit for preforms can be positioned between the sterilizing unit and the container-producing apparatus if the preforms are supplied cold to the sterilizing unit.

Figure 3:
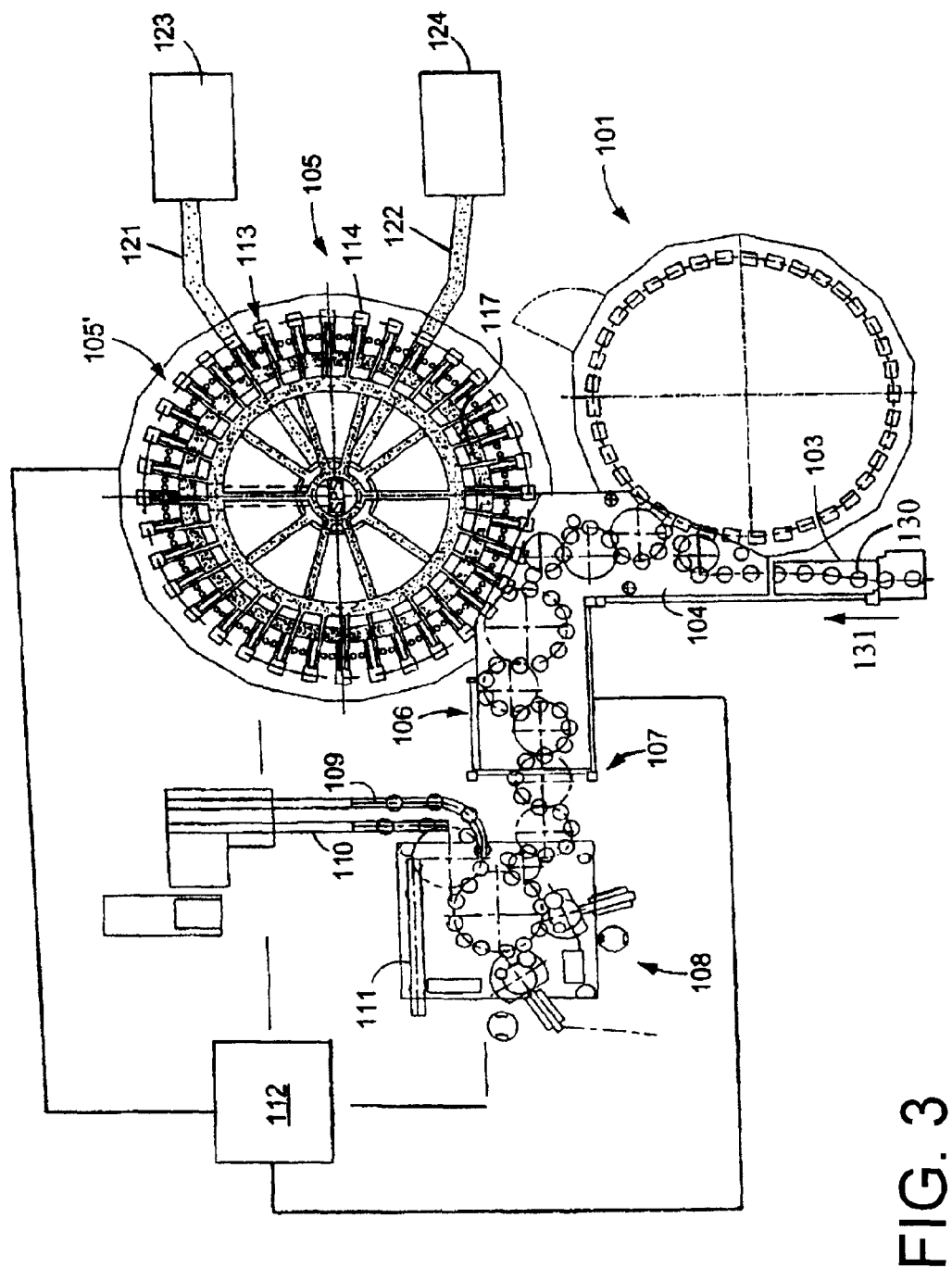
FIG. 3 shows schematically the main components of one possible embodiment example of a system for filling containers, for example, a beverage bottling plant for filling bottles with at least one liquid beverage, in accordance with at least one possible embodiment, in which system or plant could possibly be utilized at least one aspect, or several aspects, of the embodiments disclosed herein.

FIG. 3 shows schematically the main components of one possible embodiment example of a system for filling containers, specifically, a beverage bottling plant for filling bottles 130 with at least one liquid beverage, in accordance with at least one possible embodiment, in which system or plant could possibly be utilized at least one aspect, or several aspects, of the embodiments disclosed herein.

FIG. 3 shows a rinsing arrangement or rinsing station 101, to which the containers, namely bottles 130, are fed in the direction of travel as indicated by the arrow 131, by a first conveyer arrangement 103, which can be a linear conveyor or a combination of a linear conveyor and a starwheel. Downstream of the rinsing arrangement or rinsing station 101, in the direction of travel as indicated by the arrow 131, the rinsed bottles 130 are transported to a beverage filling machine 105 by a second conveyer arrangement 104 that is formed, for example, by one or more starwheels that introduce bottles 130 into the beverage filling machine 105.

The beverage filling machine 105 shown is of a revolving or rotary design, with a rotor 105', which revolves around a central, vertical machine axis. The rotor 105' is designed to receive and hold the bottles 130 for filling at a plurality of filling positions 113 located about the periphery of the rotor 105'. At each of the filling positions 103 is located a filling arrangement 114 having at least one filling device, element, apparatus, or valve. The filling arrangements 114 are designed to introduce a predetermined volume or amount of liquid beverage into the interior of the bottles 130 to a predetermined or desired level.

The filling arrangements 114 receive the liquid beverage material from a toroidal or annular vessel 117, in which a supply of liquid beverage material is stored under pressure by a gas. The toroidal vessel 117 is a component, for example, of the revolving rotor 105'. The toroidal vessel 117 can be connected by means of a rotary coupling or a coupling that permits rotation. The toroidal vessel 117 is also connected to at least one external reservoir or supply of liquid beverage material by a conduit or supply line. In the embodiment shown in FIG. 3, there are two external supply reservoirs 123 and 124, each of which is configured to store either the same liquid beverage product or different products. These reservoirs 123, 124 are connected to the toroidal or annular vessel 117 by corresponding supply lines, conduits, or arrangements 121 and 122. The external supply reservoirs 123, 124 could be in the form of simple storage tanks, or in the form of liquid beverage product mixers, in at least one possible embodiment.

As well as the more typical filling machines having one toroidal vessel, it is possible that in at least one possible embodiment there could be a second toroidal or annular vessel which contains a second product. In this case, each filling arrangement 114 could be connected by separate connections to each of the two toroidal vessels and have two individually-controllable fluid or control valves, so that in each bottle 130, the first product or the second product can be filled by means of an appropriate control of the filling product or fluid valves.

Downstream of the beverage filling machine 105, in the direction of travel of the bottles 130, there can be a beverage bottle closing arrangement or closing station 106 which closes or caps the bottles 130. The beverage bottle closing arrangement or closing station 106 can be connected by a third conveyer arrangement 107 to a beverage bottle labeling arrangement or labeling station 108. The third conveyor arrangement may be formed, for example, by a plurality of starwheels, or may also include a linear conveyor device.

In the illustrated embodiment, the beverage bottle labeling arrangement or labeling station 108 has at least one labeling unit, device, or module, for applying labels to bottles 130. In the embodiment shown, the labeling arrangement 108 is connected by a starwheel conveyer structure to three output conveyer arrangements: a first output conveyer arrangement 109, a second output conveyer arrangement 110, and a third output conveyer arrangement 111, all of which convey filled, closed, and labeled bottles 130 to different locations.

The first output conveyer arrangement 109, in the embodiment shown, is designed to convey bottles 130 that are filled with a first type of liquid beverage supplied by, for example, the supply reservoir 123. The second output conveyer arrangement 110, in the embodiment shown, is designed to convey bottles 130 that are filled with a second type of liquid beverage supplied by, for example, the supply reservoir 124. The third output conveyer arrangement 111, in the embodiment shown, is designed to convey incorrectly labeled bottles 130. To further explain, the labeling arrangement 108 can comprise at least one beverage bottle inspection or monitoring device that inspects or monitors the location of labels on the bottles 130 to determine if the labels have been correctly placed or aligned on the bottles 130. The third output conveyer arrangement 111 removes any bottles 130 which have been incorrectly labeled as determined by the inspecting device.

The beverage bottling plant can be controlled by a central control arrangement 112, which could be, for example, computerized control system that monitors and controls the operation of the various stations and mechanisms of the beverage bottling plant.

Figure 4:
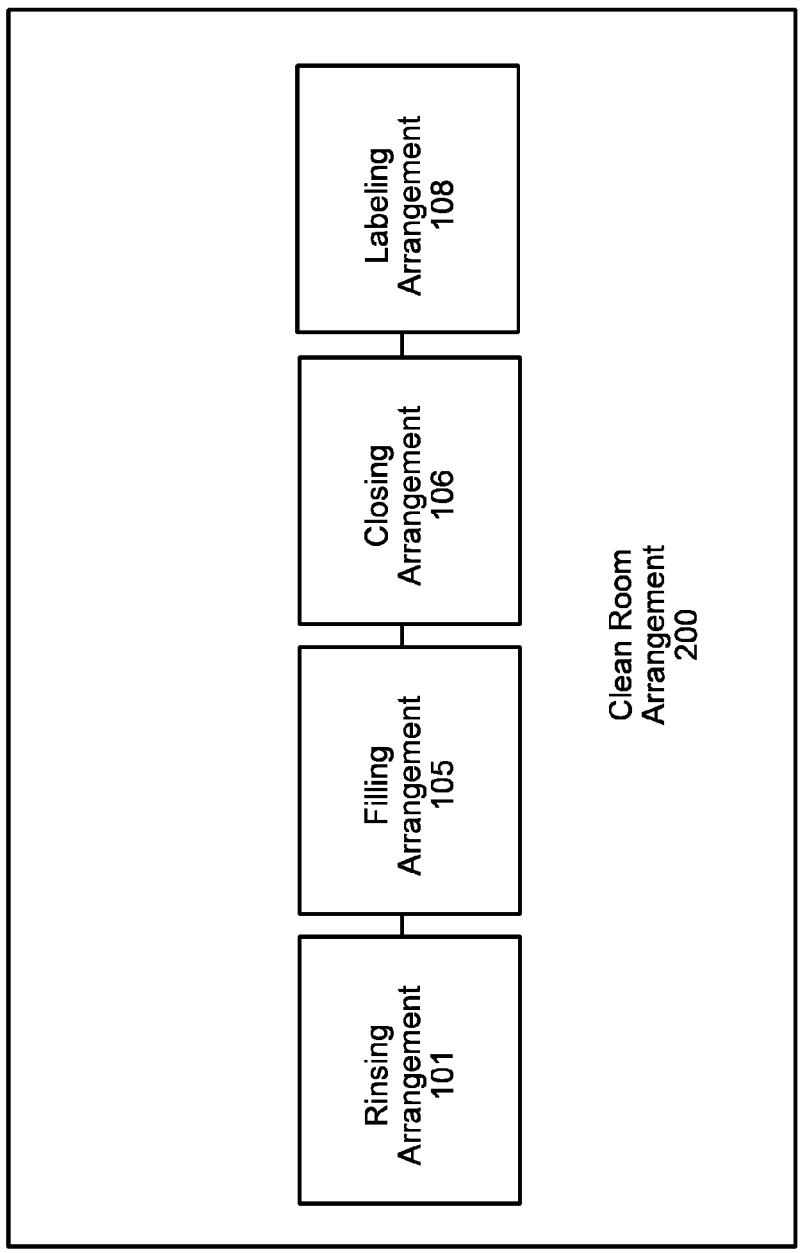
FIG. 4 shows a block diagram of a possible embodiment example of a system for filling containers with a clean room arrangement.

FIG. 4 shows a block diagram of one possible embodiment of the present application. FIG. 4 shows a rinsing arrangement 101, a filling arrangement 105, a closing arrangement 106, and a labeling arrangement 108 in a clean room arrangement 200. In one possible embodiment of the present application, the labeling arrangement 108 may be outside of the clean room arrangement 200.

Figure 5:
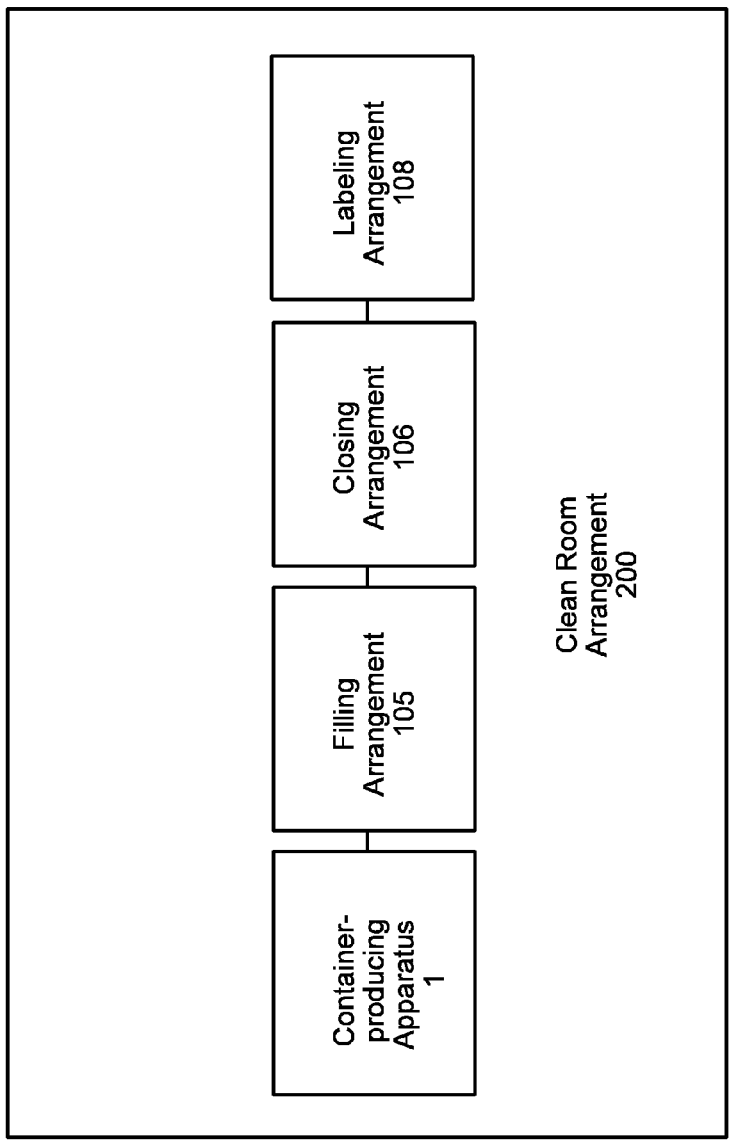
FIG. 5 shows a block diagram of a possible embodiment example of a system for filling containers with a clean room arrangement.

FIG. 5 shows a block diagram of one possible embodiment of the present application. In this embodiment, the container-producing apparatus 1, a filling arrangement 105, a closing arrangement 106, and a labeling arrangement 108 may be in a clean room arrangement 200. In one possible embodiment of the present application, the labeling arrangement 108 may be outside of the clean room arrangement 200.

The electron emitters utilized or adapted for use with at least one possible embodiment of the present application may possibly be similar to a cathode ray tube and/or how a cathode ray tube works. In a cathode ray tube, the "cathode" is a heated filament (not unlike the filament in a normal light bulb). The heated filament is in a vacuum created inside a glass "tube." The "ray" is a stream of electrons that naturally pour off a heated cathode into the vacuum.

Electrons are negative. The anode is positive, so it attracts the electrons pouring off the cathode. In a television's cathode ray tube, the stream of electrons is focused by a focusing anode into a tight beam and then accelerated by an accelerating anode. This tight, high-speed beam of electrons flies through the vacuum in the tube and hits the flat screen at the other end of the tube. This screen is coated with phosphor, which glows when struck by the beam.

There is a cathode and a pair (or more) of anodes. There is the phosphor-coated screen. There is a conductive coating inside the tube to soak up the electrons that pile up at the screen-end of the tube. The tube is wrapped in coils of wires. The steering coils are simply copper windings. These coils are able to create magnetic fields inside the tube, and the electron beam responds to the fields. One set of coils creates a magnetic field that moves the electron beam vertically, while another set moves the beam horizontally. By controlling the voltages in the coils, the electron beam can be directed at any point on the screen.

The present application relates to an apparatus for producing plastic receptacles from parisons, especially bottles, small vats, and other PET receptacles. The apparatus comprises a blow molding machine and suitable conveying devices. At least one radiation emitter is mounted on or on top of the blow molding machine, and/or a radiation emitter is directed onto at least one subarea of the blow molding machine. The present application further relates to a corresponding sterilization method for blow molding machines.

One feature or aspect of an embodiment is believed at the time of the filing of this patent application to possibly reside broadly in a container-producing apparatus for producing plastics material containers from preforms, in one possible embodiment bottles, small receptacles (kegs) and other containers made from PET, said apparatus including a blow molding machine and suitable conveying devices, wherein at least one radiation emitter is mounted at the blow molding machine or on said blow molding machine and/or a radiation emitter is directed onto at least one part region of the blow molding machine and/or at least onto a part face of the inside surfaces of the housing surrounding the container-producing apparatus.

Another feature or aspect of an embodiment is believed at the time of the filing of this patent application to possibly reside broadly in the container-producing apparatus, wherein the at least one radiation emitter is an electron emitter or UV emitter, the UV emitter in one possible embodiment being a pulsed UV emitter.

Yet another feature or aspect of an embodiment is believed at the time of the filing of this patent application to possibly reside broadly in the container-producing apparatus, wherein a plurality of identical or different radiation emitters are provided.

Still another feature or aspect of an embodiment is believed at the time of the filing of this patent application to possibly reside broadly in the container-producing apparatus, wherein the blow molding machine is a rotary blow molding machine and a radiation emitter is mounted on or is mounted at least one of the rotating elements in such a manner that said radiation emitter rotates with the element.

A further feature or aspect of an embodiment is believed at the time of the filing of this patent application to possibly reside broadly in the container-producing apparatus, wherein at least one radiation emitter is mounted on the carousel or star wheel supporting or supplying the blow molds, said radiation emitter rotating in normal operation with said carousel or star wheel.

Another feature or aspect of an embodiment is believed at the time of the filing of this patent application to possibly reside broadly in the container-producing apparatus, wherein at least one part of the surfaces of the container-producing apparatus, in one possible embodiment of the blow molding machine is designed so as to be electrostatically chargeable in order to guide electron beams in this manner.

Yet another feature or aspect of an embodiment is believed at the time of the filing of this patent application to possibly reside broadly in the container-producing apparatus, wherein at least one part of the surfaces of the container-producing apparatus, in one possible embodiment of the blow molding machine is designed so as to be positively electrostatically chargeable in order to attract electrons and/or electron beams in this manner.

Still another feature or aspect of an embodiment is believed at the time of the filing of this patent application to possibly reside broadly in the container-producing apparatus, wherein a sterilizing unit is provided upstream of the container-producing apparatus, in which sterilizing unit the preforms are sterilized upstream of the blow molding machine by means of radiation emitters.

A further feature or aspect of an embodiment is believed at the time of the filing of this patent application to possibly reside broadly in the container-producing apparatus, wherein the sterilizing unit for preforms includes radiation emitters, said radiation emitters being introducible into the opening in the preform.

Another feature or aspect of an embodiment is believed at the time of the filing of this patent application to possibly reside broadly in the container-producing apparatus, wherein the sterilizing unit is directly connected to the container-producing apparatus and in this manner sterilizing unit and container-producing apparatus form a common area, it being possible to position a hot unit for preforms between the sterilizing unit and the container-producing apparatus.

Yet another feature or aspect of an embodiment is believed at the time of the filing of this patent application to possibly reside broadly in the container-producing apparatus, wherein a filler unit is positioned downstream of the container-producing apparatus, the filler unit being directly connected to the container-producing apparatus, and sterilizing unit for preforms, container-producing apparatus and filler unit forming a substantially common area.

Still another feature or aspect of an embodiment is believed at the time of the filing of this patent application to possibly reside broadly in the container-producing apparatus, wherein a filler unit is positioned downstream of the container-producing apparatus, the filler unit being directly connected to the container-producing apparatus, and said filler unit and container-producing apparatus in this manner forming a common area.

A further feature or aspect of an embodiment is believed at the time of the filing of this patent application to possibly reside broadly in a method for producing plastics material containers from preforms, in one possible embodiment bottles, small vessels and other containers made from PET, wherein a container-producing apparatus according to one of the preceding claims is used in order to sterilize and/or to keep sterile permanently or substantially permanently at least one part of the surfaces of the container-producing apparatus and/or the at least one part of the inside surfaces of the housing surrounding the container-producing apparatus.

One feature or aspect of an embodiment is believed at the time of the filing of this patent application to possibly reside broadly in the production method, wherein a container-producing apparatus according to the present application is used, the one common area being operated as a sterile area.

Another feature or aspect of an embodiment is believed at the time of the filing of this patent application to possibly reside broadly in the production method, wherein in the transition region between filler unit, container-producing apparatus and/or the sterilizing unit for preforms, one or more locks and/or additional sterilizing steps are provided.

Yet another feature or aspect of an embodiment is believed at the time of the filing of this patent application to possibly reside broadly in the production method, wherein part of the apparatuses and of the containers is sterilized using a wet method, a wet method being used, in one possible embodiment, for the region where the upper end of said region is deeper than the openings in the preforms and/or containers and extends downwards as far as the ground.

The components disclosed in the various publications, disclosed or incorporated by reference herein, may possibly be used in possible embodiments of the present invention, as well as equivalents thereof.

The purpose of the statements about the technical field is generally to enable the Patent and Trademark Office and the public to determine quickly, from a cursory inspection, the nature of this patent application. The description of the technical field is believed, at the time of the filing of this patent application, to adequately describe the technical field of this patent application. However, the description of the technical field may not be completely applicable to the claims as originally filed in this patent application, as amended during prosecution of this patent application, and as ultimately allowed in any patent issuing from this patent application. Therefore, any statements made relating to the technical field are not intended to limit the claims in any manner and should not be interpreted as limiting the claims in any manner.

The appended drawings in their entirety, including all dimensions, proportions and/or shapes in at least one embodiment of the invention, are accurate and are hereby included by reference into this specification.

The background information is believed, at the time of the filing of this patent application, to adequately provide background information for this patent application. However, the background information may not be completely applicable to the claims as originally filed in this patent application, as amended during prosecution of this patent application, and as ultimately allowed in any patent issuing from this patent application. Therefore, any statements made relating to the background information are not intended to limit the claims in any manner and should not be interpreted as limiting the claims in any manner.

All, or substantially all, of the components and methods of the various embodiments may be used with at least one embodiment or all of the embodiments, if more than one embodiment is described herein.

The purpose of the statements about the object or objects is generally to enable the Patent and Trademark Office and the public to determine quickly, from a cursory inspection, the nature of this patent application. The description of the object or objects is believed, at the time of the filing of this patent application, to adequately describe the object or objects of this patent application. However, the description of the object or objects may not be completely applicable to the claims as originally filed in this patent application, as amended during prosecution of this patent application, and as ultimately allowed in any patent issuing from this patent application. Therefore, any statements made relating to the object or objects are not intended to limit the claims in any manner and should not be interpreted as limiting the claims in any manner.

All of the patents, patent applications and publications recited herein, and in the Declaration attached hereto, are hereby incorporated by reference as if set forth in their entirety herein.

The summary is believed, at the time of the filing of this patent application, to adequately summarize this patent application. However, portions or all of the information contained in the summary may not be completely applicable to the claims as originally filed in this patent application, as amended during prosecution of this patent application, and as ultimately allowed in any patent issuing from this patent application. Therefore, any statements made relating to the summary are not intended to limit the claims in any manner and should not be interpreted as limiting the claims in any manner.

It will be understood that the examples of patents, published patent applications, and other documents which are included in this application and which are referred to in paragraphs which state "Some examples of . . . which may possibly be used in at least one possible embodiment of the present application . . . " may possibly not be used or useable in any one or more embodiments of the application.

The sentence immediately above relates to patents, published patent applications and other documents either incorporated by reference or not incorporated by reference.

One example of a cathode ray tube, which may possibly be utilized or adapted for use in at least one possible embodiment of the present application, may possibly be found in U.S. Pat. No. 6,680,566, having the title "Television cathode ray tube," published on Jan. 20, 2004.

Some examples of linear accelerators, which may possibly be utilized or adapted for use in at least one possible embodiment of the present application, may possibly be found in the following U.S. Pat. No. 7,567,499, having the title "Sequentially pulsed traveling wave accelerator," published on Aug. 18, 2009; U.S. Pat. No. 7,599,749, having the title "Controlling a non-linear process with varying dynamics using non-linear model predictive control," published on Oct. 6, 2009; U.S. Pat. No. 7,590,219, having the title "Automatically determining a beam parameter for radiation treatment planning," published on Sep. 15, 2009; U.S. Pat. No. 7,262,566, having the title "Standing-wave electron linear accelerator," published on Aug. 28, 2007; U.S. Pat. No. 7,157,868, having the title "Linear accelerator," published on Jan. 2, 2007; U.S. Pat. No. 6,844,689, having the title "Multiple beam linear accelerator system," published on Jan. 18, 2005; and U.S. Pat. No. 6,744,226, having the title "Photoelectron linear accelerator for producing a low emittance polarized electron beam," published on Jun. 1, 2004.

The following patents, patent applications or patent publications, are hereby incorporated by reference as if set forth in their entirety herein: DE 10 2005 015 565 A1, having the following English translation of the German title "System for manufacturing of containers has process machines selectively loadable by transfer element, and has container production device formed by especially rotary stretch blow forming machine for plastic bottles," published on Oct. 12, 2006; DE 10 2004 061 230 A1, having the following in the transition of the German title "Blow molding machine for container, in particular plastic bottle, manufacture has pressure gauge to determine pressure in container and detect leakage," published on Jul. 6, 2006; and DE 295 08 864 U1, having the following German title "Blasmaschine für die Herstellung von Hohlkörpern aus Kunststoff," published on Nov. 2, 1995.

All of the patents, patent applications or patent publications, which were cited in the International Search Report dated Dec. 18, 2008, and/or cited elsewhere are hereby incorporated by reference as if set forth in their entirety herein as follows: US 2005/0118057, having the title "METHOD AND INSTALLATION FOR DECONTAMINATING PREFORM NECKS," published on Jun. 2, 2005; U.S. Pat. No. 6,562,281, having the title "METHOD FOR MAKING STERILIZED PLASTIC CONTAINERS, AND INSTALLATION THEREFOR," published on May 13, 2003; U.S. Pat. No. 6,818,068, having the title "CONVEYOR FOR TREATING HOLLOW BODIES COMPRISING AN ADVANCED PRESSURE DISTRIBUTION CIRCUIT," published on Nov. 16, 2004; WO 03/100116, having the title "METHOD AND DEVICE FOR PLASMA TREATING WORKPIECES," published on Dec. 4, 2003; and JP 2005 008243, having the following English translation of the Japanese title "ASEPTIC FILLING BLOW-MOLDED CONTAINER AND METHOD FOR STERILIZING THE CONTAINER," published on Jan. 13, 2005.

All of the patents, patent applications or patent publications, which were cited in the German Office Action dated Mar. 3, 2009, and/or cited elsewhere are hereby incorporated by reference as if set forth in their entirety herein as follows: EP 1,507,894, having the title "COATING DEVICE COMPRISING A CONVEYING DEVICE," published on Dec. 14, 2005.

All of the patents, patent applications or patent publications, which were cited in the German Office Action dated Sep. 5, 2007, and/or cited elsewhere are hereby incorporated by reference as if set forth in their entirety herein as follows: DE 10140906, having the following English translation of the German title "For cleaning out hollow plastics parisons, a jet is inserted into the hollow parison, to deliver ionized air for a given time span to remove foreign bodies and dirt particles," published on Mar. 13, 2003; DE 19520925, having the following English translation of the German title "Method for germ free filling of plastic bottles having low heat resistance using two stages of heat treatment," published on Dec. 12, 1996; DE 202006011943, having the following German title "Vorrichtung zur Sterilisation von Reinräumen für die Behandlung und/oder das Füllen and Verschliessen von Behältern," published on Apr. 12, 2007; DE 29503830, having the following German title "Handhabungsvorrichtung für in der Lebensmittel-und/oder Pharmaindustrie verwendete Gefässe bzw. deren Verschlüsse," published on Jun. 22, 1995; and DE 102005026645, having the following English edition of the German title "Ultraviolet radiation source for food irradiation or climate control has film of enhanced transparency between 250 and 270 nm arranged around the source," published on Feb. 22, 2007.

An example of an aseptic bottling system and components thereof which may possible be utilized or adapted for use in at least one possible embodiment of the present application may possibly be found in: U.S. Patent Publication 20050188651, filed Feb. 3, 2005, and having application Clüsserath; U.S. patent application Ser. No. 12/362,633, having the title "ASEPTIC BEVERAGE BOTTLE FILLING PLANT WITH A CLEAN ROOM ARRANGEMENT ENCLOSING THE ASEPTIC BEVERAGE BOTTLE FILLING PLANT AND A METHOD OF OPERATING SAME, AND AN ASEPTIC CONTAINER FILLING PLANT WITH A CLEAN ROOM ARRANGEMENT ENCLOSING THE ASEPTIC CONTAINER FILLING PLANT, AND A METHOD OF OPERATING SAME," filed on Jan. 30, 2009; and U.S. patent application Ser. No. 12/567,371, having the title "METHOD FOR THE MONITORING, CONTROL AND OPTIMIZATION OF FILLING EQUIPMENT FOR FOODS AND BEVERAGES, SUCH AS, FOR BEVERAGE BOTTLES," filed on Sep. 25, 2009.

The patents, patent applications, and patent publication listed above in the preceding seven paragraphs are herein incorporated by reference as if set forth in their entirety. The purpose of incorporating U.S. patents, Foreign patents, publications, etc. is solely to provide additional information relating to technical features of one or more embodiments, which information may not be completely disclosed in the wording in the pages of this application. Words relating to the opinions and judgments of the author and not directly relating to the technical details of the description of the embodiments therein are not incorporated by reference. The words all, always, absolutely, consistently, preferably, guarantee, particularly, constantly, ensure, necessarily, immediately, endlessly, avoid, exactly, continually, expediently, ideal, need, must, only, perpetual, precise, perfect, require, requisite, simultaneous, total, unavoidable, and unnecessary, or words substantially equivalent to the above-mentioned words in this sentence, when not used to describe technical features of one or more embodiments, are not considered to be incorporated by reference herein.

The corresponding foreign and international patent publication applications, namely, Federal Republic of Germany Patent Application No. 10 2007 017 938.5, filed on Apr. 13, 2007, having inventor Volker TILL, and DE-OS 10 2007 017 938.5 and DE-PS 10 2007 017 938.5, and International Application No. PCT/EP2008/002602, filed on Apr. 2, 2008, having WIPO Publication No. WO 2008/125216 and inventor Volker TILL, are hereby incorporated by reference as if set forth in their entirety herein for the purpose of correcting and explaining any possible misinterpretations of the English translation thereof. In addition, the published equivalents of the above corresponding foreign and international patent publication applications, and other equivalents or corresponding applications, if any, in corresponding cases in the Federal Republic of Germany and elsewhere, and the references and documents cited in any of the documents cited herein, such as the patents, patent applications and publications, are hereby incorporated by reference as if set forth in their entirety herein.

The purpose of incorporating the corresponding foreign equivalent patent application(s), that is, PCT/EP2008/002602 and German Patent Application 10 2007 017 938.5, is solely for the purpose of providing a basis of correction of any wording in the pages of the present application, which may have been mistranslated or misinterpreted by the translator. Words relating to opinions and judgments of the author and not directly relating to the technical details of the description of the embodiments therein are not to be incorporated by reference. The words all, always, absolutely, consistently, preferably, guarantee, particularly, constantly, ensure, necessarily, immediately, endlessly, avoid, exactly, continually, expediently, ideal, need, must, only, perpetual, precise, perfect, require, requisite, simultaneous, total, unavoidable, and unnecessary, or words substantially equivalent to the above-mentioned word in this sentence, when not used to describe technical features of one or more embodiments, are not generally considered to be incorporated by reference herein.

Statements made in the original foreign patent applications PCT/EP2008/002602 and DE 10 2007 017 938.5 from which this patent application claims priority which do not have to do with the correction of the translation in this patent application are not to be included in this patent application in the incorporation by reference.

Any statements about admissions of prior art in the original foreign patent applications PCT/EP2008/002602 and DE 10 2007 017 938.5 are not to be included in this patent application in the incorporation by reference, since the laws relating to prior art in non-U.S. Patent Offices and courts may be substantially different from the Patent Laws of the United States.

All of the references and documents, cited in any of the documents cited herein, are hereby incorporated by reference as if set forth in their entirety herein. All of the documents cited herein, referred to in the immediately preceding sentence, include all of the patents, patent applications and publications cited anywhere in the present application.

The description of the embodiment or embodiments is believed, at the time of the filing of this patent application, to adequately describe the embodiment or embodiments of this patent application. However, portions of the description of the embodiment or embodiments may not be completely applicable to the claims as originally filed in this patent application, as amended during prosecution of this patent application, and as ultimately allowed in any patent issuing from this patent application. Therefore, any statements made relating to the embodiment or embodiments are not intended to limit the claims in any manner and should not be interpreted as limiting the claims in any manner.

The details in the patents, patent applications and publications may be considered to be incorporable, at applicant's option, into the claims during prosecution as further limitations in the claims to patentably distinguish any amended claims from any applied prior art.

The purpose of the title of this patent application is generally to enable the Patent and Trademark Office and the public to determine quickly, from a cursory inspection, the nature of this patent application. The title is believed, at the time of the filing of this patent application, to adequately reflect the general nature of this patent application. However, the title may not be completely applicable to the technical field, the object or objects, the summary, the description of the embodiment or embodiments, and the claims as originally filed in this patent application, as amended during prosecution of this patent application, and as ultimately allowed in any patent issuing from this patent application. Therefore, the title is not intended to limit the claims in any manner and should not be interpreted as limiting the claims in any manner.

The abstract of the disclosure is submitted herewith as required by 37 C.F.R. §1.72(b). As stated in 37 C.F.R. §1.72 (b):

A brief abstract of the technical disclosure in the specification must commence on a separate sheet, preferably following the claims, under the heading "Abstract of the Disclosure." The purpose of the abstract is to enable the Patent and Trademark Office and the public generally to determine quickly from a cursory inspection the nature and gist of the technical disclosure. The abstract shall not be used for interpreting the scope of the claims.

Therefore, any statements made relating to the abstract are not intended to limit the claims in any manner and should not be interpreted as limiting the claims in any manner.

The embodiments of the invention described herein above in the context of the preferred embodiments are not to be taken as limiting the embodiments of the invention to all of the provided details thereof, since modifications and variations thereof may be made without departing from the spirit and scope of the embodiments of the invention.

What is claimed is:

1. A container-producing arrangement comprising:
   a blow-molding machine being configured to form containers from plastic preforms;
   a conveying arrangement being configured to move plastic preforms and containers;
   at least one radiation emitter being disposed at, on, or adjacent said blow-molding machine; and
   at least one of (A) and (B):
   (A) said at least one radiation emitter being disposed to direct radiation onto a substantial portion of said blow-molding machine to permit sterilization thereof; and
   (B) said at least one radiation emitter being disposed to direct radiation onto at least one portion of at least one inside surface of a housing disposed to surround the container producing arrangement to permit sterilization thereof.

2. The container-producing arrangement according to claim 1, wherein:
   said at least one radiation emitter comprises a plurality of radiation emitters comprising at least one of: ultraviolet light emitters, pulsed ultraviolet light emitters, and electron emitters, wherein either some or all of said plurality of radiation emitters are identical or different;
   said blow-molding machine comprises a rotary blow-molding machine comprising rotatable components; and
   at least one of said radiation emitters is mounted at or on a corresponding one of said rotatable components and is configured to be moved along a rotational path of movement with its rotatable component.

3. The container-producing arrangement according to claim 2, wherein:
   said conveying arrangement comprises a rotatable carousel and at least one rotatable star wheel configured to move at least one of preforms and containers along a path of rotation; and
   at least one of said radiation emitters is mounted on at least one of: said carousel and said star wheel.

4. The container-producing arrangement according to claim 3, wherein:
   the container-producing arrangement is configured to produce containers comprising bottles, small receptacles, and small kegs, which containers comprise PET plastic; and
   one of (C) and (D):
   (C) at least one part of the surfaces of the container-producing apparatus or of the blow-molding machine is configured to be positively electrostatically charged to guide electron beams thereto; and
   (D) at least one part of the surfaces of the container-producing apparatus or of the blow-molding machine is configured to be positively electrostatically charged to attract electrons and/or electron beams.

5. The container-producing arrangement according to claim 4, in combination with a sterilizing unit comprising additional radiation emitters configured to sterilize preforms prior to movement into said blow-molding machine, which said additional radiation emitters of said sterilizing unit are configured to be moved into the interiors of preforms through openings therein.

6. The combination according to claim 5, in further combination with a container filler unit positioned downstream of and connected to said container-producing arrangement, wherein said container filler unit, said sterilizing unit, and said container-producing arrangement are disposed in a common area.

7. The combination according to claim 6, in further combination with a preform heating unit disposed between said sterilizing unit and said container-producing arrangement, wherein said container filler unit, said sterilizing unit, said preform heating unit, and said container-producing arrangement are disposed in said common area.

8. The container-producing arrangement according to claim 2, wherein:
said rotary carousel comprises a plurality of container handling devices disposed about the periphery thereof; and
at least one of said radiation emitters is disposed adjacent the periphery of said rotary carousel and to emit radiation toward said container handling devices, and is configured to move with a container handling device over a portion of the rotational path of movement of the container handling device to direct an increased amount of radiation toward the container handling device to increase the sterilization thereof.

9. The container-producing arrangement according to claim 1, wherein:
said conveying arrangement comprises a rotatable carousel and at least one rotatable star wheel configured to move at least one of preforms and containers along a path of rotation; and
said at least one radiation emitter comprises a plurality of radiation emitters, wherein at least one of said radiation emitters is mounted on at least one of: said carousel and said star wheel.

10. The container-producing arrangement according to claim 1, wherein said at least one radiation emitter comprises a plurality of radiation emitters disposed to emit radiation toward and to sterilize a substantial portion of at least one of: said blow-molding machine, and the inside surfaces of a housing disposed to surround the container-producing arrangement.

11. The container-producing arrangement according to claim 1, wherein said at least one radiation emitter comprises a plurality of radiation emitters disposed to emit radiation toward and to sterilize a substantial portion of said blow-molding machine and a substantial portion of the inside surfaces of a housing disposed to surround the container-producing arrangement.

12. A method of producing containers with a container-producing arrangement, said method comprising the steps of:
forming containers from plastic preforms with a blow-molding machine;
moving plastic preforms and containers with a conveying arrangement; and
emitting radiation from at least one radiation emitter disposed at, on, or adjacent said blow-molding machine, wherein said step of emitting radiation comprises at least one of (A) and (B):
(A) directing radiation onto a substantial portion of said blow-molding machine and sterilizing the substantial portion; and
(B) directing radiation onto at least one portion of at least one inside surface of a housing disposed to surround the container-producing arrangement and sterilizing the at least one portion.

13. The method according to claim 12, wherein:
said method further comprises sterilizing the preforms in a sterilizing unit prior to blow-molding;
said step of moving preforms and containers comprises moving preforms and containers with one of a rotatable carousel and a rotatable star wheel;
said method further comprises filling the containers in a container filler unit; and
operating said container filler unit, said sterilizing unit, and said container-producing arrangement are disposed in a common area under sterile conditions.

14. The method according to claim 13, wherein said step of operating under sterile conditions comprises using at least one lock or other sterilizing device at transition regions between said sterilizing unit and said container-producing arrangement, and between said container-producing arrangement and said container filler unit.

15. The method according to claim 14, wherein said step of using at least one lock or other sterilizing device at transition regions comprises wet sterilizing solely those portions of said common area, said container filler unit, said sterilizing unit, or said container-producing arrangement which are disposed below openings in said preforms or containers in order to wet sterilize those portions without introducing wet sterilizing media into said preforms or containers.

16. The method according to claim 12, wherein:
said step of emitting radiation comprises emitting radiation from a plurality of radiation emitters comprising at least one of: ultraviolet light emitters, pulsed ultraviolet light emitters, and electron emitters, wherein either some or all of said plurality of radiation emitters are identical or different;
said step of forming containers from plastic preforms with a blow-molding machine comprises forming containers with a rotary blow-molding machine; and
said step of moving preforms and containers comprises moving preforms and containers with one of a rotatable carousel and a rotatable star wheel of said rotary blow-molding machine.

17. The method according to claim 16, wherein:
said step of forming containers from plastic preforms comprises forming bottles, small receptacles, and/or small kegs, from PET plastic preforms; and
said method further comprises:
emitting radiation from a movable one of said radiation emitters disposed adjacent the periphery of said rotary carousel toward one of a plurality of container handling devices disposed about the periphery of said rotary carousel; and
moving said movable radiation emitter with the container handling device over a portion of the rotational path of movement of the container handling device to direct an increased amount of radiation toward the container handling device to increase the sterilization thereof.

18. The method according to claim 12, wherein said method comprises emitting radiation from a plurality of emitters toward and sterilizing a substantial portion of at least one of: said blow-molding machine, and the inside surfaces of a housing disposed to surround the container-producing arrangement.

19. The method according to claim 12, wherein said method comprises emitting radiation toward and sterilizing a substantial portion of said blow-molding machine and a substantial portion of the inside surfaces of a housing disposed to surround the container-producing arrangement.

* * * * *